US010956538B2

United States Patent
Mirov

(10) Patent No.: US 10,956,538 B2
(45) Date of Patent: Mar. 23, 2021

(54) LOW-POWER SYSTEMS AND METHODS FOR DETERMINING MEASUREMENT TIMES OF VALUES OBTAINED BY A MEASURING DEVICE

(71) Applicant: Verily Life Sciences LLC, Mountain View, CA (US)

(72) Inventor: Russell Mirov, Los Altos, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 540 days.

(21) Appl. No.: 15/809,225

(22) Filed: Nov. 10, 2017

(65) Prior Publication Data

US 2018/0157803 A1 Jun. 7, 2018

Related U.S. Application Data

(60) Provisional application No. 62/429,731, filed on Dec. 3, 2016.

(51) Int. Cl.
*A61B 5/00* (2006.01)
*G06F 19/00* (2018.01)
(Continued)

(52) U.S. Cl.
CPC ........ *G06F 19/3468* (2013.01); *A61B 5/0002* (2013.01); *A61B 5/0015* (2013.01);
(Continued)

(58) Field of Classification Search
CPC ............. G06F 19/3468; G06F 19/3406; G06F 5/0031; G06F 5/1459; G06F 5/1473;
(Continued)

(56) References Cited

U.S. PATENT DOCUMENTS 6,216,096 B1  4/2001 Obermeier
6,356,161 B1 * 3/2002 Nolan .................... H03K 3/011
                                                       331/111
(Continued)

FOREIGN PATENT DOCUMENTS

WO  2017/189970 A1  11/2017

OTHER PUBLICATIONS

International Search Report and Written Opinion from the International Searching Authority dated Feb. 2, 2018, or International Application No. PCT/US2017/063509, filed Nov. 28, 2017, 12 pages.

*Primary Examiner* — Chu Chuan Liu
(74) *Attorney, Agent, or Firm* — Christensen O'Connor Johnson Kindness PLLC

(57) ABSTRACT

The present disclosure relates to a low-power measuring device. In one implementation, the low-power measuring device includes a first sensor for measuring a first value, the first value being a measurement of a variable, and a counter unit for generating a first counter value indicative of a first elapsed time since the first value is measured by the first sensor. The low-power measuring device further includes at least one processor configured to send the first value to a remote apparatus, send the first counter value to the remote apparatus, cause the remote apparatus to determine the first elapsed time based on the first value and the first counter value, and cause the remote apparatus to determine a first obtained time at which the first value is measured by the first sensor based on the determined first elapsed time and a reference time of the remote apparatus.

17 Claims, 7 Drawing Sheets

(51) Int. Cl.
*G16H 40/63* (2018.01)
*A61B 5/1459* (2006.01)
*A61B 5/1473* (2006.01)
*A61B 5/1477* (2006.01)
*A61M 5/315* (2006.01)
*A61B 5/145* (2006.01)

(52) U.S. Cl.
CPC .......... *A61B 5/0031* (2013.01); *A61B 5/1459* (2013.01); *A61B 5/1473* (2013.01); *A61B 5/1477* (2013.01); *A61B 5/4839* (2013.01); *A61B 5/6849* (2013.01); *A61M 5/31511* (2013.01); *G16H 40/63* (2018.01); *A61B 5/14532* (2013.01); *A61B 2560/0209* (2013.01); *A61B 2560/0214* (2013.01); *A61B 2560/0252* (2013.01); *A61B 2562/028* (2013.01); *A61M 5/31568* (2013.01); *A61M 2205/3306* (2013.01); *A61M 2205/3317* (2013.01); *A61M 2205/3368* (2013.01); *A61M 2205/3592* (2013.01); *A61M 2205/8212* (2013.01)

(58) Field of Classification Search
CPC .. G06F 5/1477; G06F 5/6849; G06F 5/31511; G06F 5/0015; G06F 5/14532; A61B 2560/0209; A61B 2560/0214; A61B 2560/028; A61B 2560/0252
See application file for complete search history.

(56) References Cited

U.S. PATENT DOCUMENTS

| | | |
|---|---|---|
| 2005/0192846 A1 | 9/2005 | De Zwart et al. |
| 2006/0224335 A1 | 10/2006 | Borleske et al. |
| 2009/0163793 A1 | 6/2009 | Koehler et al. |
| 2013/0072771 A1* | 3/2013 | Gu ........................ A61B 5/0205 600/324 |
| 2015/0174342 A1 | 6/2015 | Mitrosky et al. |
| 2015/0372681 A1* | 12/2015 | Melanson ............... H03L 1/028 331/1 R |
| 2016/0030683 A1* | 2/2016 | Taylor ............... A61M 5/14248 604/151 |
| 2016/0226443 A1 | 8/2016 | Caffee et al. |

* cited by examiner

LOW-POWER SYSTEMS AND METHODS FOR DETERMINING MEASUREMENT TIMES OF VALUES OBTAINED BY A MEASURING DEVICE

REFERENCE TO RELATED APPLICATION

This application claims benefit to U.S. Provisional Application No. 62/429,731, filed on Dec. 3, 2016, the contents of which are incorporated herein by reference.

BACKGROUND

The present disclosure relates to systems and methods for determining measurement times of values obtained by a measuring device, such as a medical device. More specifically, and without limitation, the present disclosure relates to systems and methods for remotely determining times at which values are measured by a medical device.

A variety of medical devices exist, including those that are used for administering drugs to a patient, such as insulin. Measuring the quantity and recording the timing of a drug's administration is an integral part of many medical treatments. For many treatments, to achieve the best therapeutic effect, specific quantities of the drug may need to be injected at specific times of the day. For example, individuals suffering from diabetes may be required to inject themselves regularly throughout the day in response to measurements of their blood glucose. The frequency and volume of insulin injections must be carefully tracked and controlled to keep the patient's blood glucose level within a healthy range.

Medication injection devices, such as glucose injection syringes and pens, have been developed in this area. However, it is often impractical to include components needed to generate accurate timestamps for tracking when the medication was injected. Components needed to generate timestamps are typically too large to incorporate into the injection device and/or consume too much power. Thus, developing portable, medication injection devices that automatically track drug administration is challenging. What is needed is the ability to accurately determine the time at which measurements are made by a medical device that is too small or unable to incorporate the needed components for generating accurate timestamps.

SUMMARY

The present disclosure relates to systems and methods for determining measurement times of values obtained by a measuring device, such as a medical device. More specifically, and without limitation, the present disclosure relates to systems and methods for remotely determining times at which values are measured or otherwise obtained by a medical device.

In accordance with one example embodiment, an apparatus is provided that includes a storage medium storing a set of instructions. The apparatus also includes at least one processor that is configured with the set of instructions to receive a first value from a measuring device. The first value may represent a variable obtained by the measuring device. The at least one processor may be further configured to receive a first counter value from the measuring device. The first counter value may be generated by a counter unit of the measuring device and indicative of a first elapsed time between a reference time and a first obtained time of the first value. Further, the first obtained time may be a time at which the first value is obtained by the measuring device. In addition, the at least one processor may be further configured to determine the first elapsed time represented by the first counter value as function of the first value and determine the first obtained time of the first value based on the determined first elapsed time and the reference time.

In accordance with another example embodiment, a method is provided for determining obtained times of received values. The method includes receiving a first value from a measuring device. The first value may represent a variable obtained by the measuring device. The method further includes receiving a first counter value from the measuring device. The first counter value may be generated by a counter unit of the measuring device and indicative of a first elapsed time between a reference time and a first obtained time of the first value. The first obtained time may be a time at which the first value is obtained by the measuring device. The method also includes determining the first elapsed time represented by the first counter value as function of the first value and determining the first obtained time of the first value based on the determined first elapsed time and the reference time.

In accordance with yet another example embodiment, a monitoring system is provided that includes a storage medium that stores a set of instructions. The system also includes at least one processor that is configured by the set of instructions to receive a first measured value from a measuring device. The first measured value may be a variable measured by the measuring device. The at least one processor may be further configured determine a received time representing when the first measured value is received from the measuring device and receive a first counter value from the measuring device. The first counter value may be generated by a counter unit of the measuring device and indicative of a first elapsed time between the received time and a first measurement time of the first measured value. Further, the first measurement time may be a time at which the first measured value is measured by the measuring device. In addition, the at least one processor may be further configured to calculate the first elapsed time represented by the first counter value as function of the first measured value and calculate the first measurement time of the first measured value based on the determined first elapsed time and the received time.

In accordance with another example embodiment, a low-power measuring device is provided that includes a first sensor for measuring a first value, the first value being a measurement of a variable, and a counter unit for generating a first counter value indicative of a first elapsed time since the first value is measured by the first sensor. The low-power measuring device further includes at least one processor configured to send the first value to a remote apparatus, send the first counter value to the remote apparatus, cause the remote apparatus to determine the first elapsed time based on the first value and the first counter value, and cause the remote apparatus to determine a first obtained time at which the first value is measured by the first sensor based on the determined first elapsed time and a reference time of the remote apparatus.

Before explaining example embodiments of the present disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be utilized as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXAMPLE EMBODIMENTS

Embodiments of the present disclosure provide improved systems and methods for remotely determining times at which values are measured or otherwise obtained by a medical device. In accordance with some embodiments, the medical device may send to a remote apparatus or monitoring system a measured value and information that can be used to determine the elapsed time between when the measured value is obtained by the medical device and when the measured value is received at the remote apparatus or system. The remote apparatus or system may use the received information and the time at which the measured value is received to determine the time at which the measured value is measured or otherwise obtained by the medical device. Additionally, the measured value may be used to improve the accuracy of determining the measurement time.

Reference will now be made in detail to the embodiments implemented according to the disclosure, the examples of which are illustrated in the accompanying drawings. Wherever possible, the same reference numbers will be used throughout the drawings to refer to the same or like parts.

Reference will now be made in detail to the embodiments implemented according to the disclosure, the examples of which are illustrated in the accompanying drawings. Wherever possible, the same reference numbers will be used throughout the drawings to refer to the same or like parts.

Figure 1:
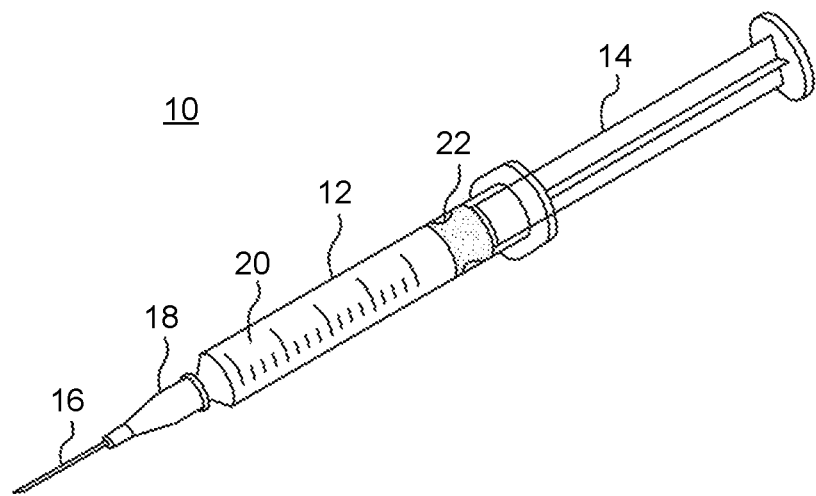
FIG. 1 is a perspective view of a medical device comprising a syringe, which includes a plunger head, according to an example embodiment.

FIG. 1 shows a perspective view of a medical device comprising a syringe 10, according to an example embodiment of the present disclosure. Syringe 10 may be designed to administer a medication 20, like insulin. As shown in FIG. 1, syringe 10 includes a barrel 12, a plunger 14, a needle 16, and a hub 18 connecting needle 16 to barrel 12. Barrel 12 may contain medication 20 and syringe 10 may be configured to dispense medication 20 from needle 16 when plunger 14 is depressed. A standard syringe usually contains a plunger head at the end of the plunger that seals the top of the barrel and forces the fluid out the needle when the plunger is depressed. The plunger head for a standard syringe is usually just a piece of molded rubber.

For syringe 10 shown in FIG. 1, the standard plunger head has been replaced with a smart or intelligent plunger head 22, consistent with embodiments of the present disclosure. As further disclosed herein, plunger head 22 includes electronics to measure and register the quantity of medication 20 administered by syringe 10. In some embodiments, plunger head 22 may be installed by withdrawing plunger 14 and removing a standard plunger head (if present) and installing plunger head 22. Further, in some embodiments, syringe 10 may be manufactured and supplied with a smart plunger head 22 preinstalled. Plunger head 22 may be sized to correspond with the size of barrel 12. For example, plunger head 22 may be formed to fit any size of syringe. For instance, plunger head 22 may be sized to fit a 1 ml, 2 ml, 3 ml, 5 ml, 10 ml, 20 ml, 30 ml, or 50 ml syringe.

Figure 2:
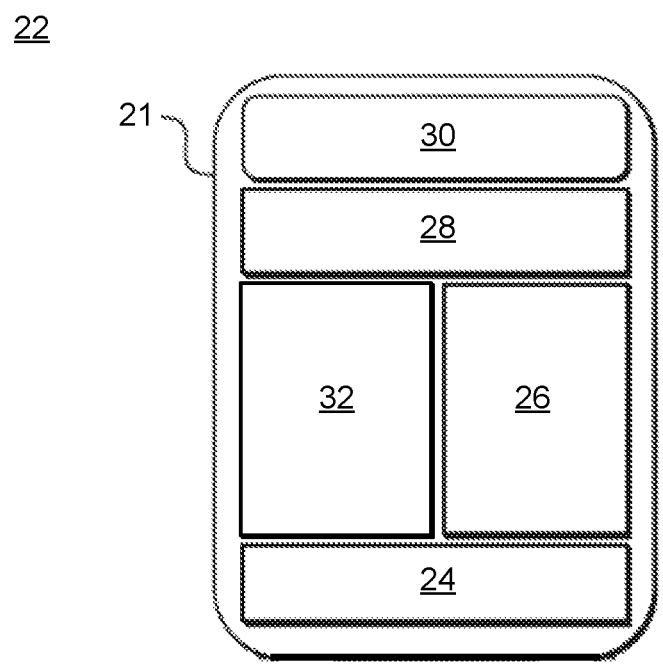
FIG. 2 is a schematic representation of an intelligent plunger head of FIG. 1, according to an example embodiment.

FIG. 2 is a schematic illustration of plunger head 22, according to an example embodiment. As shown in FIG. 2, plunger head 22 may include a number of components, including a transducer 24, a microcontroller 26, a power source 28, and an antenna (e.g., for near field communication (NFC)) or a transceiver 30 (e.g., for BLUETOOTH low energy (BLE) communication). In some embodiments, transceiver 30 may include or incorporate an antenna (not shown). As shown in FIG. 2, plunger head 22 may also include a temperature sensor 32. Temperature sensor 32 may be configured to measure a temperature of plunger head 22, which may be affected by the ambient temperature and/or temperature of medication 20. In some embodiments, additional or other sensors may be provided to measure one or more variables. In addition to temperature values, examples of other measured or obtained variables include voltage, current, linear acceleration, angular acceleration, amplitude of sound, light intensity, and gas mixture. Examples of other types of sensors include an accelerometer, a gyroscope, a microphone, a light sensor, and a gas sensor.

Transducer 24 may be configured to send and receive ultrasonic signals, and generate an output reflecting, for example, the transmission and receipt of such signals. Microcontroller 26 may be programmed with instructions to control the overall operation of the components of plunger head 22. Transceiver 30 may be configured to wirelessly communicate with a remote apparatus or monitoring system (e.g., a smart phone, a glucose monitor, an insulin pump, or a computer) using one or more wireless communication methods. The one or more wireless communication methods may include, for example, radio data transmission, Bluetooth, BLE, near field communication (NFC), infrared data transmission, electromagnetic induction transmission, and/ or other suitable electromagnetic, acoustic, or optical transmission methods. Power source 28 may be configured to power transducer 24, microcontroller 26, transceiver 30, temperature sensor 32, and other electronical components of plunger head 22.

In some embodiments, as shown in FIG. 2, the components of plunger head 22 may be encapsulated (in part or fully) by an elastomer 21 (e.g., rubber, ethylene propylene (EPM), Nitrile (NBR), ethylene propylene diene (EPDM), polybutadiene, or polisoprene) that is shaped to define plunger head 22. In some embodiments, elastomer 21 may be formed using a molding process involving pouring of hot, liquid elastomer over the components to be encapsulated. The overall shape of plunger head 22 may be cylindrical and approximately match the interior diameter of barrel 12 of syringe 10. Moreover, plunger head 22 may include an upper end that is in contact with the distal end of plunger 14 within barrel 12 of syringe 10, and lower end that comes into contact within fluid in barrel 12 and cooperates with plunger 14 to dispense fluid from syringe 10.

Figure 3:
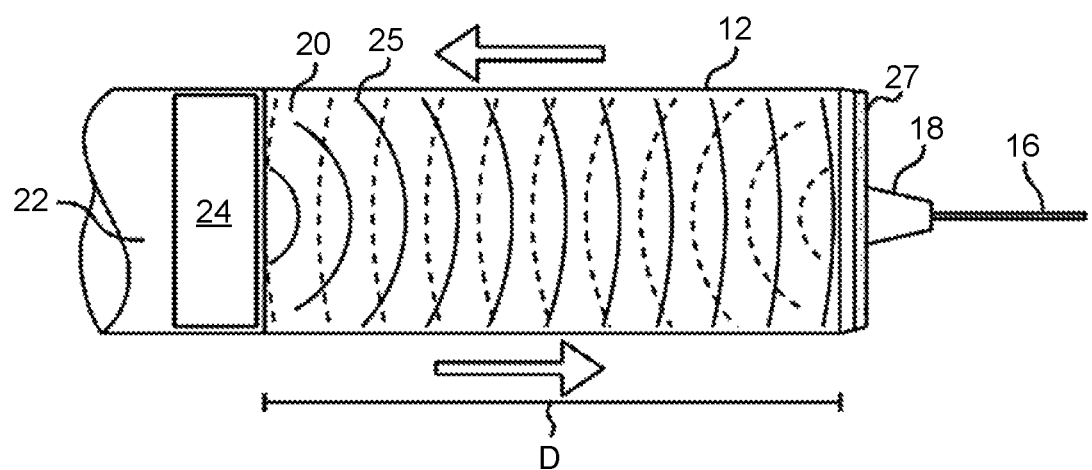
FIG. 3 illustrates the behavior of ultrasonic signals transmitted by the example plunger head of FIG. 1.

Transducer 24 may include an actuator, piezoelectric element, and/or speaker-like voice coil. Further, as noted above, transducer 24 may generate and send a pressure wave or ultrasonic signal. Transducer 24 may be sized to be smaller than the inner diameter of barrel 12 and, as noted above, encapsulated in an elastomer 21. As shown in FIG. 3, transducer 24 may generate ultrasonic signals 25 (e.g., radiated sound energy waves) and send the ultrasonic signals 25 down barrel 12 toward hub 18 and needle 16. The ultrasonic signals can travel through medication 20 along the length of barrel 12 and bounce or reflect off an end 27 of barrel 12 and travel back through medication 20 to plunger head 22. The reflected ultrasonic signals can be received and detected by transducer 24. The speed of sound in medication 20 and other fluids may be a known value (and stored in memory of microcontroller 26) and thus a distance D can be calculated accurately based on the time it takes for a ultrasonic signal to travel down and back from transducer 24. As plunger head 22 is moved down barrel 12, distance D will change and by knowing the diameter of barrel 12 the volume of medication 20 dispensed may be calculated based on the change in distance D.

In some embodiments, microcontroller 26 may be attached to a printed circuit board (PCB) and may include one or more processors, including for example, a central processing unit (CPU). The processor(s) may be implemented using a commercially available processor or may be a custom designed processor (e.g., an application-specific integrated circuit (ASIC)). Microcontroller 26 may include additional components including, for example, non-volatile memory (e.g., a flash memory), volatile memory (e.g., a random access memory (RAM)), and other like components, configured to store programmable instructions and data.

In some embodiments, microcontroller 26 is programmed with a set of instructions to control the operation of transducer 24 and other components of plunger head 22. For example, microcontroller 26 may be programmed with instructions to receive output signals from transducer 24 and calculate the quantity of medication 20 dispensed based on the ultrasonic signals 25 generated by transducer 24. In some embodiments, microcontroller 26 may be programmed to detect and record the reflection times of the ultrasonic signals 25. Based on the reflection times, microcontroller 26 may track and produce a time profile and/or other data reflecting the position of transducer 24 (i.e., plunger head 22). Based on the time profile of the position, microcontroller 26 may be able to identify a first distance $D_1$ or starting position (e.g., before medication 20 is dispensed), which may correspond with barrel 12 being filed and a second distance $D_2$ or ending position (e.g., after medication 20 is dispensed), which may correspond with barrel 12 being empty. Microcontroller 26 may then calculate the change in distance between $D_1$ and $D_2$ and based on the change in distance calculate the volume (i.e., amount or quantity) of medication 20 dispensed. In some embodiments, microcontroller 26 may be programmed to take into account signal delays between microcontroller 26 and transducer 24 for the calculation of distance D.

In some embodiments, microcontroller 26 may include a counter unit. The counter unit may be configured to generate counter values, which will be discussed below with respect to FIGS. 4-6. The counter unit may include an oscillator such as an RC oscillator. Additionally, or alternatively, the counter unit may include an LC oscillator and/or a micro-electro-mechanical systems (MEMS) oscillator. In some embodiments, the counter unit may be separate from microcontroller 26. For example, the counter unit may be electrically coupled to microcontroller 26. In some embodiments, a portion of the counter unit may be separate from microcontroller 26. For example, the portion of the counter unit including an oscillator may be separate from microcontroller 26, but a program to generate counter values using the oscillator may be included in microcontroller 26.

In some embodiments, a second microcontroller may be programmed with a set of instructions to control the operation of transducer 24 and other components of plunger head 22. In some embodiments, the second microcontroller may be a part of transducer 24. For example, the processor may be fabricated in the same substrate as transducer 24 so as to reduce the electrical parasitics between the processor and transducer 24. In these embodiments, the processor send calculated distance D, volume of medication 20 dispensed, and/or volume of medication 20 remaining to microcontroller 26. Plunger head 22 may transmit data (e.g., the amount of medication 20 dispensed and time and date it was dispensed) to a remote apparatus or system (e.g., a smart phone, a glucose monitor, an insulin pump, or a computer) via one or more of the wireless communication methods.

Antenna or transceiver 30 may be used to communicate with a variety of remote devices and systems (e.g., smart phones, glucose monitors, insulin pumps, computers, etc.). Plunger head 22 may transmit the information via any suitable wireless communication method. For example, in some embodiments, plunger head 22 may utilize radio data transmission, BLUETOOTH or (BLE), near field communication (NFC), infrared data transmission or other suitable method. In some embodiments, information may also be wirelessly transmitted from a remote apparatus or system to plunger head 22 via antenna 30. For example, the date and time may be set by writing to microcontroller 26 via the wireless communication.

Power source 28 may be any suitable power source. For example, power source 28 may be a battery, a capacitor, or the like. In some embodiments, power source 28 may be a non-rechargeable battery that is configured to last the storage and operational life of plunger head 22. For example, in some embodiments, power source 28 may be a conventional small-sized battery (e.g., a watch battery).

Figure 4:
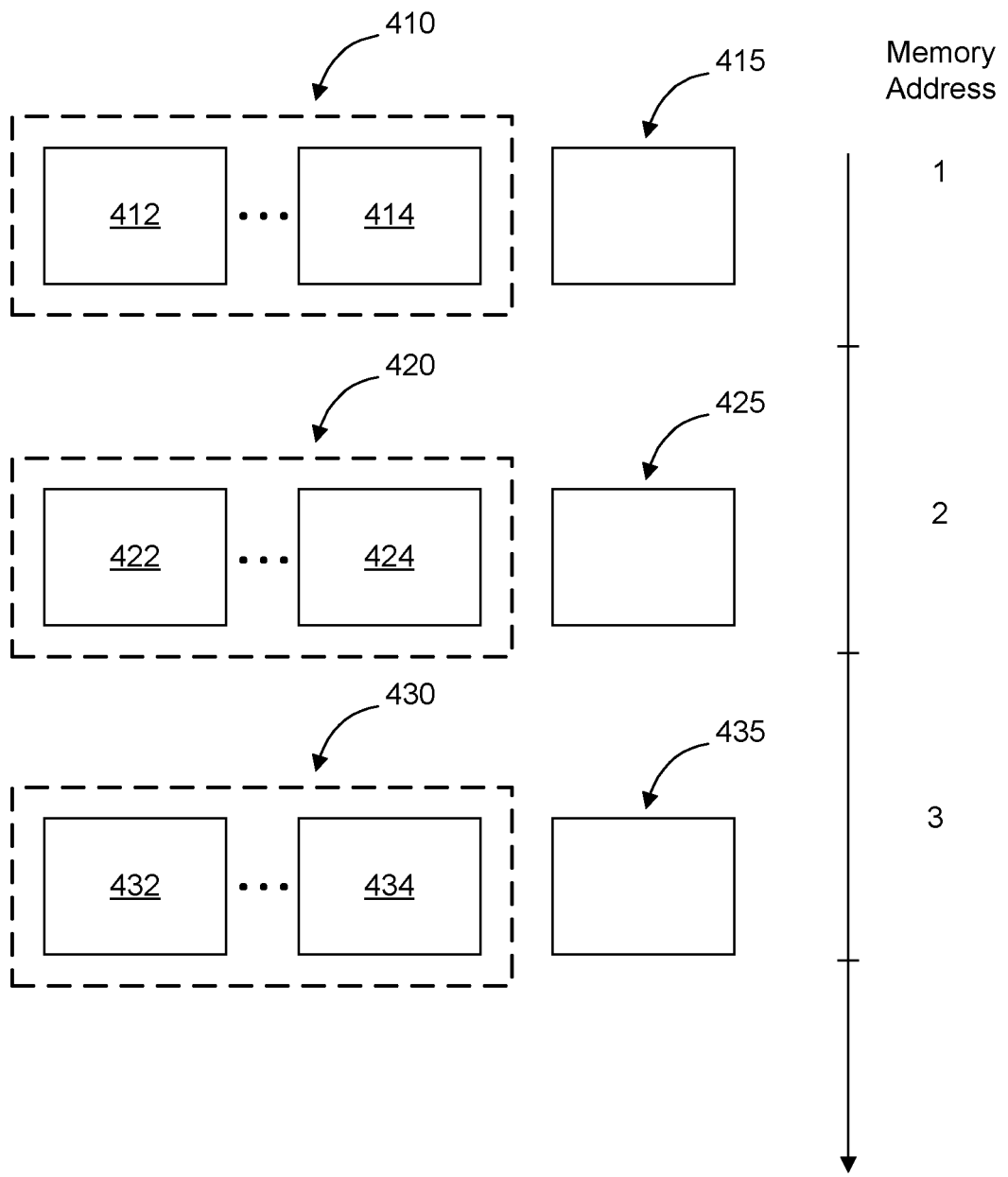
FIG. 4 illustrates a partial content of a memory of a microcontroller, according to an example embodiment.

FIG. 4 illustrates a partial content of a memory 400 of microcontroller 26 of a measuring device such as syringe 10 in accordance with an example embodiment. As discussed above, memory 400 may be included in microcontroller 26. Alternatively, memory 400 may be external and electrically connected to microcontroller 26. A measuring device may be any device configured to take measurements, for example, using sensors or sensing circuits.

In FIG. 4, memory 400 is shown to store a number of data sets, each including one or more pieces of data. For example, memory 400 is storing a first data set 410 including at least data 412 and data 414, a second data set 420 including at least data 422 and data 424, and a third data set 430 including at least data 432 and data 434.

In some embodiments, a piece of data in a data set may be a sensor data obtained using a sensor of syringe 10. A sensor data may represent, for example, ambient temperature that is measured using temperature sensor 36 or distance D measured using transducer 24. Other examples of a sensor data include motion data measured using one or more inertial sensors (e.g., gyroscope and accelerometer) and/or orientation data measured using one or more orientation sensors (e.g., magnetic sensor). Additionally, or alternatively, a sensor data may include data from one or more optical sensors (e.g., indicative of opacity of medication 20) and/or one or more radio components (e.g., indicative of syringe's 10 proximity to another radio device). The sensor data may be raw data obtained from a sensor or processed data derived from the raw data. For example, the sensor data may represent a volume, or a change in the volume, of medication 20 remaining in syringe 10. Such data may be derived from one or more values of distance D measured using transducer 24.

Additionally, or alternatively, a piece of data in a data set may be any data that may be otherwise available to microcontroller 26. For example, a piece of data may represent a voltage or a current level that can be sensed by a sensing circuit of microcontroller 26 (or a sensing circuit electrically coupled to microcontroller 26). In another example, a piece of data may be generated by microcontroller 26.

According to some embodiments, memory 400 may further store data representing a counter value associated with each data set. In FIG. 4, for example, memory 400 may store a first counter value 415 associated with first data set 410, a second counter value 425 associated with second data set 420, and a third counter value 435 associated with third data set 430.

In some embodiments, a data structure may be used to keep track of which counter value is associated with which data set. Alternatively, or additionally, the associated counter value may be stored immediately between the next data set. In some embodiments, a counter value may be associated with one or more pieces of data in the data set instead of being associated with the data set itself.

In some embodiments, a counter value may be indicative of and may be used to determine the elapsed time between when two data sets are considered to have been obtained by microcontroller 26 of syringe 10. Alternatively, or additionally, for a counter value associated with the last data set, the counter value may be indicative of and may be used to determine the elapsed time between when a data set considered to have been obtained by microcontroller 26 and when the counter value is read from memory 400 of microcontroller 26. The elapsed time between when two data sets are considered to have been obtained by microcontroller 26 and the elapsed time between when a data set considered to have been obtained by microcontroller 26 and when the counter value is read from memory 400 of microcontroller 26 are both hereinafter referred to as "the elapsed time."

A data set may be considered to have been obtained by microcontroller 26, for example, when the first piece of data in the data set is obtained by microcontroller 26, when the last piece of data in the data set is obtained by microcontroller 26, or at a time between when the first and last pieces of data in the data set are obtained by microcontroller 26. The time at which a data set is considered to have been obtained by microcontroller 26 is hereinafter referred to as "the obtained time of a data set." A piece of data may be "obtained" by microcontroller 26, for example, when the data becomes available at microcontroller 26 (e.g., when the data is received at an I/O port of microcontroller 26) or when the data is written to memory 400.

In some embodiments, the determination of the elapsed times using counter values may be performed by microcontroller 26 of syringe 10. Alternatively, as described below with respect to FIGS. 5 and 6, the counter values, among other things, may be sent to a remote apparatus or system, and a processor of the remote apparatus or system may determine the elapsed times by processing, among other things, the received counter values. In some embodiments, the counter values and/or data sets may be sent to the remote apparatus or system, and the process of the remote apparatus or system may determine the elapsed times by processing the received counter values and data sets as well as information that may be available to the remote apparatus or system (but not readily available to microcontroller 26 of syringe 10). That is, the remote apparatus or system may determine the elapsed times represented by the received counter values. Further, the determination of the elapsed times may be function of one or more information available to the remote apparatus or system.

In the example of FIG. 4, counter value 415 may be indicative of and may be used to determine the elapsed time between the obtained time of data set 410 and the obtained time of data set 420. Similarly, counter value 425 may be indicative of and may be used to determine the elapsed time between the obtained times of data set 420 and the obtained time of next data set 430. The obtained times of data set 410, data set 420, and data set 430 may be equal to, for example, times at which data 412, data 422, and data 433 are written to memory 400, respectively. For the counter value associated with the last data set (e.g., data set 430 and counter value 435), the stored counter value may be repeatedly updated by microprocessor 26 so as to represent data that is indicative of and may be used to determine the elapsed time between when the counter value is read from memory 400 and the obtained time of the last data set.

In some embodiments, a counter value may be a number that is proportional to the elapsed time. Therefore, in these embodiments, a constant of proportionality may be used in conjunction with the counter value to determine the elapsed time. For example, the counter value may be multiplied by the constant of proportionality to calculate the elapsed time.

In some embodiments, a counter value that is proportional to the elapsed time may be generated based on a periodic signal available to microcontroller 26. A counter value may be generated to represent a number of cycles of a periodic signal that has elapsed between when the two data sets are obtained by microcontroller 26 or between when a data set is obtained by microcontroller 26 and when the counter value is read from memory 400 of microcontroller 26. Thus, in these embodiments, the constant of proportionality may be the period of the periodic signal. In some embodiment, the period of the periodic signal may be, for example, 30 seconds, 1 minute, 5 minutes, or 10 minutes.

The periodic signal may be generated by a counter unit of microcontroller 26. As discussed above, the counter unit may include an oscillator, which may be an RC oscillator. RC oscillators may be less accurate, but use less power, than crystal oscillators. In some embodiments, the counter unit may include an LC oscillator and/or a MEMS oscillator.

According to some embodiments, however, the counter value may not be perfectly proportional to the elapsed time because of non-idealities. Instead, the counter value may be approximately proportional to the elapsed time. In one example where the counter value is generated based on an oscillator, the non-idealities include drifting of the period of the periodic signal from the initial period (i.e., the expected period), for example, due to a change in ambient temperature and/or the voltage applied to the oscillator. Therefore, when the counter value is multiplied by the expected period to calculate the elapsed time, the calculated elapsed time may be different from the actual elapsed time. Other factors that may cause the period of the periodic signal to drift include aging of the oscillator and acceleration experienced by the oscillator (for MEMS oscillator), to provide some examples. Non-idealities also include, for example, component-to-component variation caused by the manufacturing process. The degree in which various factors affect the periodic signal may be experimentally determined.

In some embodiments, one or more pieces of data of data sets may be used to improve the accuracy of the calculated elapsed time. For example, as discussed above, a change in ambient temperature and/or the voltage applied to the oscillator may cause a drift in the period of the signal generated by the oscillator. In some embodiments, one or more pieces of data in data sets may include measured values of ambient temperature and/or the voltage applied to the oscillator. In these embodiments, the stored data of data sets may be used in the calculation of the elapsed time to improve accuracy.

In some embodiments, an increase in the voltage applied to the oscillator and/or ambient temperature may cause the period of signal generated by the oscillator to increase or decrease, depending on the design of the oscillator circuit. In these embodiments, the sensed voltage applied to the oscillator and/or the measured ambient temperature may be used to compensate for the changes to the period of the oscillator.

For example, in some embodiments, the measurement system's RC oscillator will have its frequency shift over time as a factor of temperature and voltage. As shown here, the sensor systems record data along with temperature and voltage—and the data is time stamped (with the relatively imprecise RC oscillator counter value) as it is uploaded to a host system. The host system will know precisely when it received the data and that knowledge can be applied to the most recent sensor readings. If any older readings are also transferred, the timestamp uncertainty may grow as the time elapsed increases. The host system can utilize its knowledge of the RC oscillator's behavior under different voltage and temperature conditions to undo those effects. The host system may do this by inserting the temperature and voltage into a behavior function and calculate backwards starting from the very latest synchronization timestamp (a time that is precisely known by the host system).

The relationship between the voltage applied to the oscillator, the ambient temperature, and the period of the oscillator may be determined experimentally during the manufacturing process and/or may be determined based on the characterization data obtained from the designer/manufacturer of the oscillator. In some embodiments, the relationship may be represented using one or more correlation coefficients between, e.g., the voltage applied to the oscillator, the ambient temperature, and the period of the oscillator. In some embodiments, the correlation coefficients may be determined for each oscillator or for a batch of oscillators (i.e., an averaged value). In some embodiments, the correlation coefficients may be stored in the measuring device. In these embodiments, the measuring device may send the stored correlation coefficients to a remote apparatus or system, which may use the received correlation coefficients to compensate for the changes in the period of the oscillator. In some embodiments, the correlation coefficients may be stored in the remote apparatus or system.

In FIG. 4, for example, counter value 415 may be generated based on a signal generated by an RC oscillator. The expected period of the generated signal may be period T, and counter value 415 may represent a number of cycles of the periodic signal that has elapsed between the obtained times of data set 410 and data set 420. Further, data 412 and data 414 of data set 410 may represent ambient temperature and a voltage across the RC oscillator measured/sensed at one time, respectively, and data 422 and data 424 of data set 420 may represent a ambient temperature and a voltage across the RC oscillator measured/sensed at another time, respectively. In this example, the elapsed time between the obtained times of data set 410 and data set 420 may be calculated using counter value 415; at least one of data 412, data 414, data 422, and data 424; and the expected period of the generated signal. More specifically, a corrected period may be calculated using the expected period, and data 412, 414, 422, and/or 424, and the corrected period may be multiplied by counter value 415 to calculate the elapsed time.

In some embodiments, two or more counter values excluding the last counter value may be the same. In these embodiments, memory 400 may store a counter value associated with the multiple data sets. In some embodiments, the counter value associated with the multiple data sets may be programmed as a constant or a variable of a program executing on a processor.

In some embodiments, instead of a counter value, a time stamp may be associated with each data set. In these embodiments, the time stamp may include the obtained time of each data set. That is, unlike a counter value, which may need further processing to determine the obtained time, a time stamp includes the obtained time. To generate a time stamp for each data set, syringe 10 (or microcontroller 26) may include and maintain a real-time clock (RTC) that keeps track of the current time-of-day and/or date. In some embodiments, the RTC may be calibrated by a crystal oscillator, which may be included in syringe 10 and electrically coupled to microcontroller 26. Maintaining the RTC (and operating the crystal oscillator) in syringe 10, however, increases power consumption. Therefore, in embodiments where a battery is used as power source 28 for syringe 10, maintaining the RTC in syringe 10 may adversely affect its the operational life time. (The amount of power used to generate and store the counter value for each data set may be less than the amount of power used to maintain the RTC and generate a time stamp for each data set.) Further, the size of syringe 10 that includes the RTC may be larger than the size of syringe 10 that does not include the RTC.

According to the disclosed embodiments, the data sets and/or the associated counter values are stored in memory 400 such that the information pertaining to the order in which the data sets and/or the counter values are stored in memory 400 of microcontroller 26 and/or obtained by microcontroller 26 is preserved. In some embodiments, such information may be preserved by sequentially storing the data sets in memory 400 in the order the data sets and/or counter values are obtained by microprocessor 26. For example, in FIG. 4, first data set 410 is obtained before second data set 420 and second data set 420 before third data set 430 by microprocessor 26. Therefore, microcontroller 26 may store first data set 410 at address 1 of memory 400, second data set 420 at address 2 of memory 400, and third data set 430 at address 3 of memory 400. In some embodiments, the information pertaining to the order in which the data sets are stored may be preserved by using a data structure capable of tracking the order. For example, the data sets and/or the counter values may be stored in a data structure that associates a numerical value to each data set and/or the counter value. Further, the numerical value may be increased for each new data set stored in memory 400. Therefore, to determine the order in which the data sets are stored, the numerical values associated with data sets may be retrieved and compared/sorted, for example.

Figure 5:
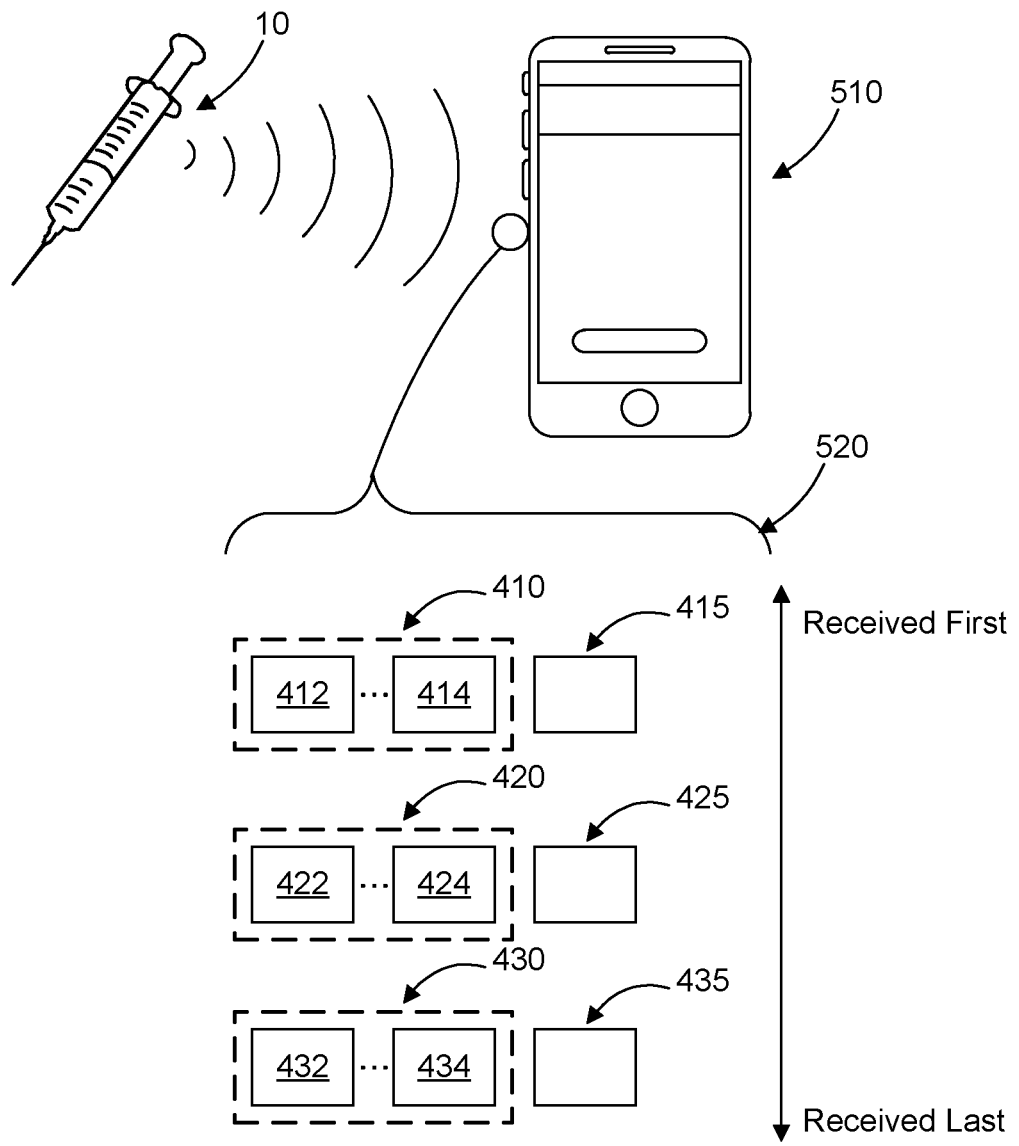
FIG. 5 illustrates a remote apparatus configured to receive data from the medical device of FIG. 1, according to an example embodiment.

FIG. 5 illustrates a remote apparatus 510 configured to receive data 520 from a measuring device such as syringe 10 according to an example embodiment. Remote apparatus 510 in FIG. 5 may further be configured to determine the obtained times of the received data sets or pieces of data within the data sets (i.e., times at which data sets or pieces of data within the data sets are obtained by microcontroller 26 of syringe 10).

FIG. 5 also illustrates an example content of received data 520 at remote apparatus 510. As shown in FIG. 5, received data 520 includes at least some of the content of memory 400 of syringe 10's microcontroller 26. For example, received data 520 includes data sets 410, 420, and 430 and counter values 415, 425, and 435.

In some embodiments, remote apparatus 510 may a portable electronic device. For example, remote apparatus 510 may be a cellular phone, a tablet, a laptop, or a personal computer. Alternatively, remote apparatus 510 may be a dedicated device (e.g., a medical device for use at a physician's office) configured to pair with syringe 10 and configured to receive and process data 520 from syringe 10. According to some embodiments, remote apparatus 510 may include at least one processor. In some embodiments, syringe 10 may communicate with remote apparatus 510 using transceiver 30.

As discussed above, the data sets and/or the associated counter values may be stored in memory 400 such that the information pertaining to the order in which the data sets and/or the counter values are obtained by microcontroller 26 and/or stored in memory 400 of microcontroller 26 is preserved. To that end, microcontroller 26 of syringe 10 may be configured to send the data sets and/or the counter values to remote apparatus 510 such the same information is preserved. In some embodiments, microcontroller 26 of syringe 10 may be configured to send the data sets and/or counter values to remote apparatus 510 in the order that the data sets and/or the counter values are obtained by microcontroller 26 and/or stored in memory 400 of microcontroller 26. Additionally, or alternatively, the processor of remote apparatus 510 may be configured to receive the data sets and/or counter values in the order they are obtained by microcontroller 26 and/or stored in memory 400 of microcontroller 26. In FIG. 5, for example, remote apparatus 510 is shown to receive the data sets and counter values in the same order in which they are stored in memory 400 of microcontroller 26. Alternatively, or additionally, syringe 10 may send the data sets and/or the counter values in one or more data structures that enables remote apparatus 510 to determine the order in which the received data sets and/or counter values have been obtained by microcontroller 26 and/or stored in memory 400 of microcontroller 26, even when the data sets and/or counter values are received at remote apparatus 510 in a random order.

According to some embodiments, remote apparatus 510 may include and maintain an RTC, which keeps track of the current time-of-day and date. The RTC may be calibrated using an oscillator such as a crystal oscillator. Alternatively, the RTC may be calibrated using another time source such as a timing server accessible by the remote apparatus 510. In some embodiments, the RTC may be also used by other functions of remote apparatus 510.

In some embodiments, the RTC may be used by the processor of remote apparatus 510 to determine the times at which data sets (or one or more pieces of data in data sets) and/or counter values are received at remote apparatus 510. Additionally, or alternatively, the RTC may be used by the processor of remote apparatus 510 to determine the times at which data sets and/or counter values are stored in a memory of remote apparatus 510.

In some embodiments, the RTC may be used by the processor of remote apparatus 510 to determine the time at which a piece of data (or a data set) is read from memory 400 of microcontroller 26 or transmitted from syringe 10 by taking into account the delay between when the piece of data (or the data set) is read or transmitted and when the data is received at remote apparatus 510. In some embodiments, the such delay may be negligible and the times at which the piece of data (or the data set) is read or transmitted from syringe 10 and received at remote apparatus 510 may be substantially the same.

Figure 6:
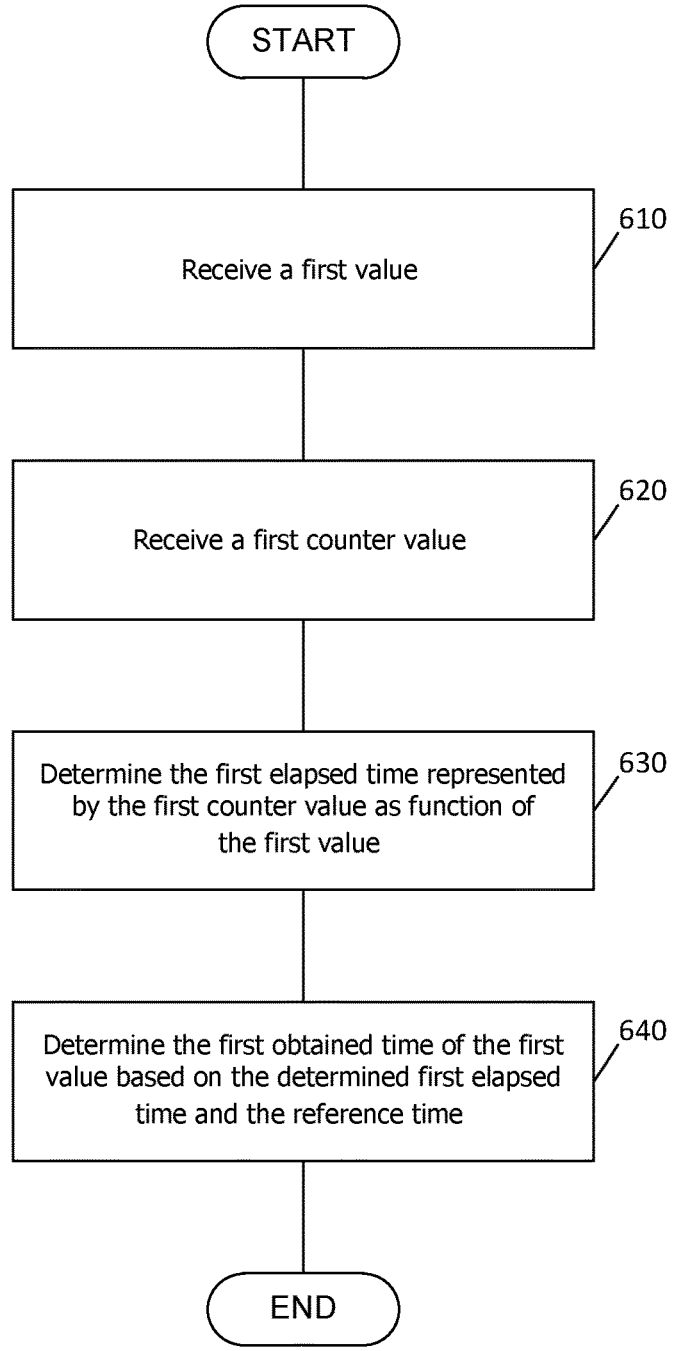
FIG. 6 illustrates a flow diagram of a process for determining the obtained times of the received data sets performed by the apparatus of FIG. 5, according to an example embodiment.

FIG. 6 illustrates a flow diagram of a process 600 for determining the obtained times of the received data sets (or data within the data sets) performed by remote apparatus 510 of FIG. 5 or a similarly constructed monitoring system, according to an example embodiment. In some embodiments, as discussed above, remote apparatus 510 may be a portable device.

At step 610, the processor of remote apparatus 510 may receive a first value (e.g., data 432 or data 434) from a measuring device, such as syringe 10. In some embodiments, the measuring device may be a wearable device or a tracking device (e.g., inertial navigation unit). In other embodiments, the measuring device may be a weather station or any Internet of Things (IOT) device. For example, a measuring device may be a weather station configured to measure humidity, temperature, light intensity, and/or wind speed at a remote location. In some embodiments, the first value may represent a variable obtained by syringe 10. For example, the first received value may represent a data measured using one or more sensors of syringe 10, such as ambient temperature measured using temperature sensor 36 of syringe 10. Alternatively, or additionally, the first received value may represent any data that is otherwise available to microcontroller 26 of syringe 10, such as a voltage sensed using a sensing circuit.

In some embodiments, as shown in FIG. 5, the processor of remote apparatus 510 may receive the first value as a part of a data set. For example, the processor of remote apparatus 510 may receive, from syringe 10, data 432 and/or data 434 as a part of receiving data set 430. In some embodiments, the data set associated with the first received value may be the data set that is stored last in memory 400 or the data set that is obtained last at microcontroller 26.

In some embodiments, the data set associated with the first received value may further include any other data that may be available to microcontroller 26. For example, the data set associated with the first received value may further include distance D of FIG. 3, a data representing a volume of medicine 20 remaining in syringe 10, or a data representing an injection volume.

At step 620, the processor of remote apparatus 510 may receive a first counter value from syringe 10. The first counter may be generated by a counter unit of syringe 10. Further, the first counter may be indicative of a first elapsed time between a reference time and a first obtained time of the first value (or the data set that includes the value). The first obtained time may be a time at which the first value is obtained by syringe 10.

As discussed above, a data set may be considered to have been obtained by syringe 10's microcontroller 26, for example, when the first piece of data in the data set is obtained by syringe 10's microcontroller 26, when the last piece of data in the data set is obtained by syringe 10's microcontroller 26, or at a time between when the first and last pieces of data in the data set are obtained by syringe 10's microcontroller 26.

The reference time may represent a time at which the first value (or the data set associated with the first received value) is received from syringe 10. In other embodiments, the reference time may represent a time at which the first value (or the data set associated with the first received value) is transmitted by syringe 10 or read from memory 400 of microcontroller 26 of syringe 10.

As discussed above, the differences between the time at which a value (or the data set associated with the value) is received from syringe 10, a time at which the value (or the data set associated with the value) is transmitted by syringe 10, and the time at which the value (or the data set associated with the value) is read from memory 400 of microcontroller 26 of syringe 10 may be negligible. The reference time may be determined using, for example, the RTC of remote apparatus 510, which may maintain the current time-of-day and date.

In some embodiments, remote apparatus 510 may further include a wireless transceiver. Further, remote apparatus 510 may receive the first value and the first counter value wirelessly from the measuring device.

At step 630, the processor of remote apparatus 510 may determine the first elapsed time represented by the first counter value as function of the first value.

In some embodiments, the first counter value may be a number that is proportional to the first elapsed time between the reference time and when the first value (or the data set that includes the first value) is obtained by microcontroller 26 of syringe 10. In these embodiments, the first value may be a measured value of a variable that may affect the proportionality of the first elapsed time and the first counter value. Therefore, the determination of the first elapsed time using the first value in addition to the first counter value may yield a more accurate calculated first elapsed time compared to the first elapsed time calculated without the first value.

In some embodiments, the first counter value may be generated based on a periodic signal available to microcontroller 26 of syringe 10 (e.g., using an RC oscillator). For example, the periodic signal may be generated by a counter unit of syringe 10. As discussed above, the counter unit may be included, external, or partially included in microcontroller 26. In these embodiments, the first counter value may be generated to represent a number of cycles of a periodic signal that has elapsed between the reference time and when the first value (or the data set that includes the first value) is obtained by microcontroller 26 of syringe 10. Thus, in these embodiments, the constant of proportionality may be the period of the periodic signal.

In some embodiments, the period of the periodic signal may be estimated experimentally. For example, the period of the periodic signal may be estimated by measuring a period of the periodic signal generated by the oscillator included or to be included in each manufactured syringe 10. Alternatively, or additionally, the estimated period of the periodic signal may be determined by averaging the measured periods of a batch of oscillators. In some embodiments, the estimated period of the periodic signal may be obtained from the designer/manufacturer of the oscillator.

The experimentally determined period of the periodic signal may not be exact for several reasons. First, component-to-component variation of the oscillator, for example due to process variations, may cause the period of the periodic signal to be offset from the intended value. Second, the period of the signal generated by the oscillator may also be affected by variables that change while syringe 10 is being used. For example, the period of the signal generated by the oscillator may be positively or negatively correlated (linearly or non-linearly) to the ambient temperature and/or the voltage applied to the oscillator. In one implementation, for example, the period of the signal may decrease linearly when the ambient temperature or the voltage applied to the oscillator is increased.

Therefore, in some embodiments, the first value may be a measured value of a variable that may affect the variability of the period of the periodic signal. As discussed above, variables that may affect the variability of the period of the periodic signal include, for example, ambient temperature and/or the voltage applied to the oscillator used to generate the periodic signal.

In some embodiments, the determination of the first elapsed time may include determining a corrected period of the periodic signal based the first value, and multiplying the corrected period with the first counter value. In some embodiments, the determination of the first elapsed time may include determining an approximate elapsed time based on the first counter value and correcting the approximate elapsed time based on the received first value to determine the first elapsed time.

At step 640, the processor of remote apparatus 510 may determine the first obtained time of the first value based on the determined first elapsed time and the reference time. In some embodiments, the determination of the first obtained time may include subtracting the determined first elapsed time from the reference time.

At a first optional step, the processor of remote apparatus 510 may receive a second value from syringe 10. In some embodiments, the second value may represent the variable measure or obtained by syringe 10 at a different time than the first value.

At a second optional step, the processor of remote apparatus 510 may receive a second counter value from syringe 10. The second counter value may be generated by the counter unit of syringe 10. Further, the second counter may be indicative of a second elapsed time between the first obtained time of the first value and a second obtained time of the second value. The second obtained time may be a second time at which the second value is obtained by syringe 10.

At a third optional step, the processor of remote apparatus 510 may determine the second elapsed time represented by the second counter value as function of at least one of the first value and the second value.

At a fourth optional step, the processor of remote apparatus 510 may determine the second obtained time of the second value based on the determined second elapsed time and the first obtained time of the first value. In some embodiments, the determination of the second obtained time may include subtracting the second elapsed time from the first obtained time of the first value.

At a fifth optional step, the processor of remote apparatus 510 receive a first volume from the apparatus, the first volume having an obtained time substantially the same as the first obtained time of the first value. The first volume may represent one of: a volume of medication remaining in the medication injection apparatus and an injected dose.

In alternative embodiments, at step 640, the processor of remote apparatus 510 may determine the first elapsed time represented by the first counter value. In these embodiments, the determined first elapsed time may be approximate as the received first value may not have been used in the determination of the first elapsed time. In these embodiments, the determination of the first obtained time of the first value may be further based on the received first value. That is, the first obtained time of the first value may be function of the received first value. In some embodiments, the determination of the first obtained time of the first value may include determining an approximate obtained time of the first value based on the first elapsed time and correcting the approximate obtained time of the first value based on the first value.

Figure 7:
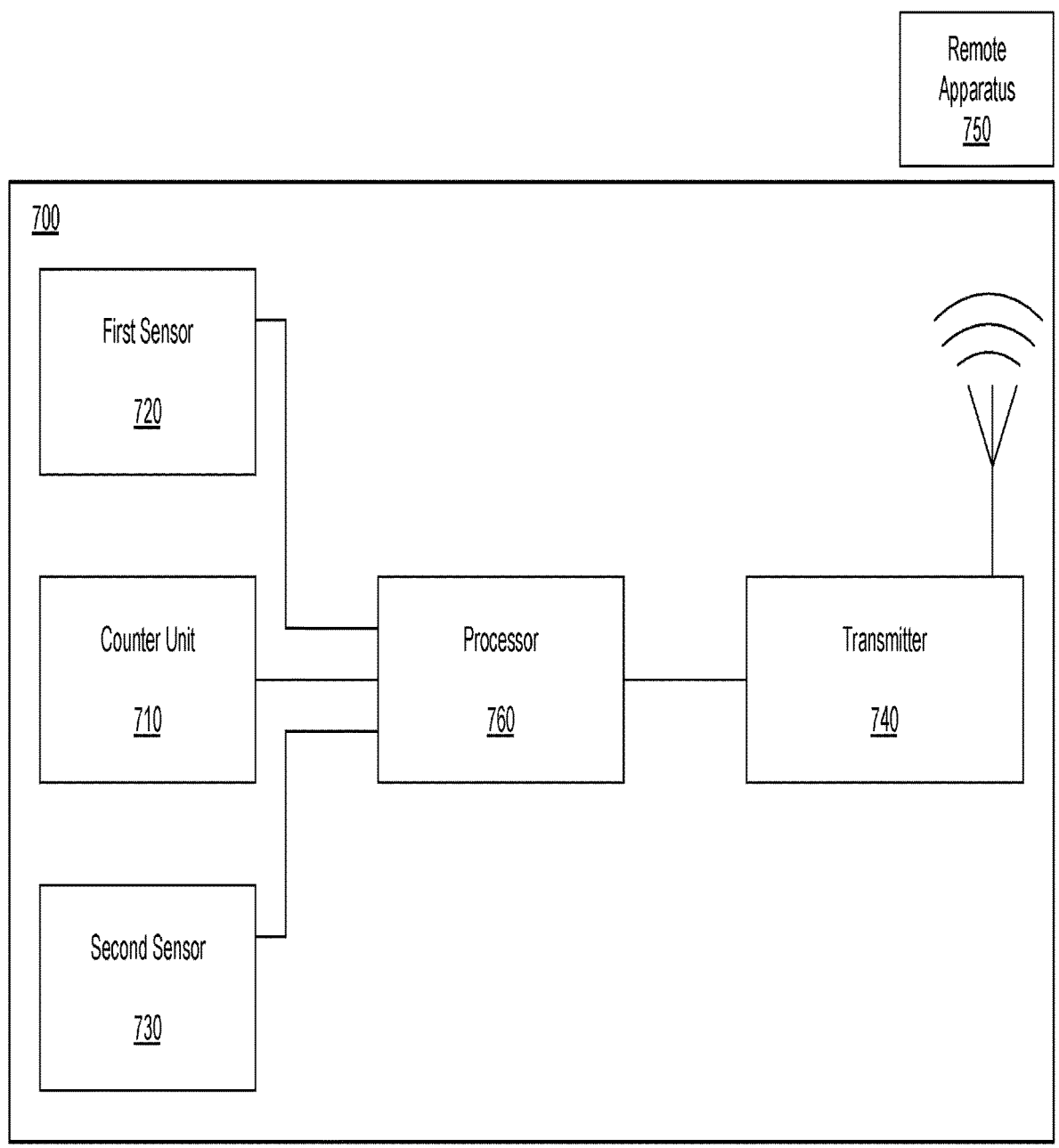
FIG. 7 illustrates an measuring device, according to an example embodiment.

FIG. 7 illustrates an example measuring device 700, according to an example embodiment. As shown in FIG. 7, measuring device 700 includes a counter unit 710 (e.g., an oscillator) for generating a counter value and a sensor 720 for measuring a first value, where the first value is a measurement of a variable.

In some embodiments, sensor 720 may be a temperature sensor for measuring ambient temperature or a voltage sensing circuit for measuring a voltage applied to counter unit 710. In some embodiments, first sensor 720 may include a plurality of sensors (e.g., a temperature sensor and a voltage sensing circuit).

Counter unit 710 is configured to generate the counter value such that the value is indicative of the elapsed time since the variable is measured by sensor 720 (e.g., the measurement time of the first value). For example, the counter value may be the number of cycles of a periodic signal generated by the oscillator has elapsed since the variable is measured (e.g., since the first value was measured). In this example, the counter value may be reset after a measurement of a variable (e.g., after the first value is measured). In some embodiments, counter unit 710 may include an oscillator such as an RC oscillator, LC oscillator, or MEMS oscillator.

As further shown in FIG. 7, measuring device 700 may also include a second sensor 730 for measuring a second value, where the second value is a measurement of another variable. In some embodiments, the second sensor may be configured to make measurements at substantially the same time as first sensor 720. Therefore, in these embodiments, the measurement time of the first value may be used as the measurement time of the second value. The second sensor may be, for example, an electrochemical sensor, an optical sensor, or an electrical sensor. The variable measured by the second sensor may include, for example, concentration of an analyte in bodily fluid such as blood, tears, interstitial fluid, or perspiration. The variable measured by the second sensor may also include voltage or current level detected at a nerve or muscle, for example.

Measuring device 700 may further include a transmitter 740 for communicating with a remote apparatus or system 750. In some embodiments, processor 760 may be configured to use transmitter 740 to send the first value, the counter value, and/or the second value to remote apparatus or system 750.

In some embodiments, measuring device 700 may be a portable device, with a battery as a power source. In such embodiments, a limited amount of power may be available to measuring device 700, and therefore, minimizing the power consumption by components of measuring device 700 may be desired. In some embodiments, measuring device 700 may be a body-mountable device. For example, measuring device 700 may be an eye-mountable device, tooth-mountable device, or skin-mountable device. In some embodiments, measuring device 700 may be an implant device that may be partially or completely implanted in a body.

In some embodiments, in place of a counter unit, measuring device 700 may include and maintain an a real-time clock (RTC) that keeps track of the current time-of-day and/or date. In some embodiments, the RTC may be calibrated by a crystal oscillator that is included in measuring device 700 and electrically coupled to processor 760. Maintaining the RTC (and operating the crystal oscillator) in measuring device 700, however, increases power consumption. Therefore, in embodiments where a battery is used as the power source for measuring device 700, maintaining the RTC in measuring device 700 may adversely affect its the operational life time. Further, the size of measuring device 700 that includes the RTC may be larger than the size of measuring device 700 that does not include the RTC.

Figure 8:
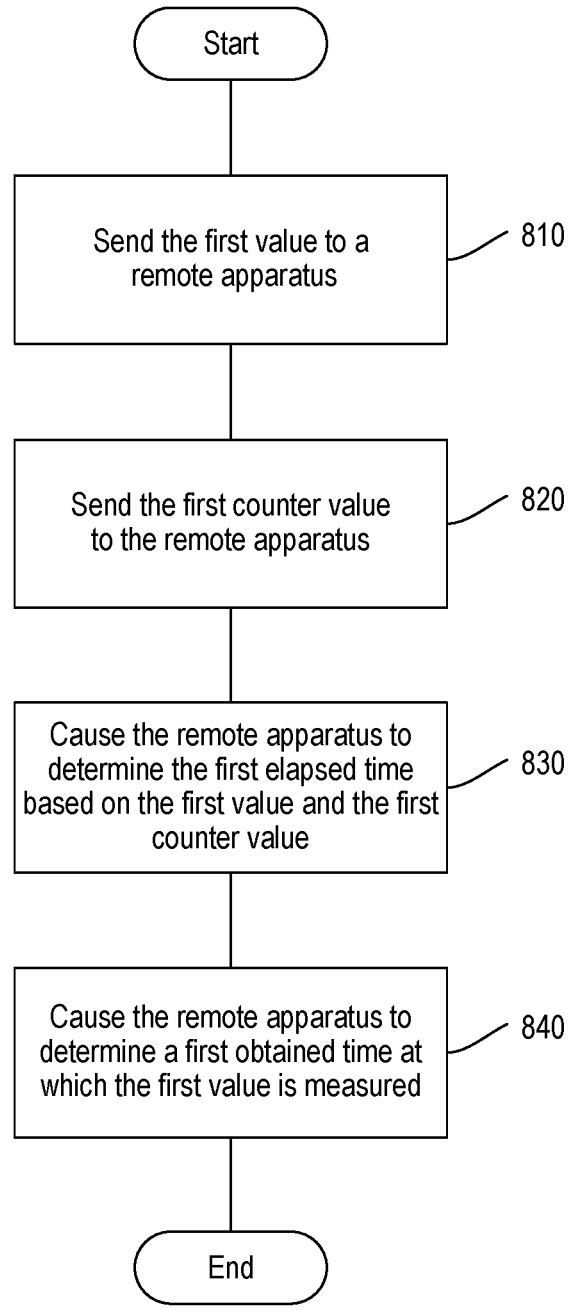
FIG. 8 illustrates a flow diagram of a process for causing a remote device to determine the obtained times of the received data sets performed by the measuring device of FIG. 7, according to an example embodiment.

FIG. 8 illustrates a flow diagram of a process 800 performed by processor 760 of measuring device 700, according to an example embodiment.

At step 810, processor 760 may use transmitter 740 to send the first value measured by first sensor 720 to remote apparatus or system 750.

At step 820, processor 760 may use transmitter 740 to send the first counter value generated by counter unit 710 to the remote apparatus or system 750.

At step 830, processor 760 may cause remote apparatus or system 750 to determine the first elapsed time based on the first value and the first counter value. In some embodiments, the sending of the first value and/or the counter value at steps 810 and/or 820 may trigger remote apparatus or system 750 to determine the first elapsed time based on the first value and the first counter value.

At step 840, processor 760 may cause remote apparatus or system 750 to determine a first obtained time at which the first value is measured by the first sensor based on the determined first elapsed time and a reference time of remote apparatus or system 750. In some embodiments, the sending of the first value and/or the counter value at steps 810 and/or 820 may trigger remote apparatus or system 750 to determine a first obtained time at which the first value is measured by the first sensor based on the determined first elapsed time and a reference time of the remote apparatus (e.g., after the completion of step 830).

At an optional step, processor 760 may use transmitter 740 to send the second value measured by second sensor 730 to remote apparatus or system 750. In some embodiments, the second value may be measured substantially at the same time as the first value.

In embodiments where measuring device 700 includes an RTC instead of counter unit 710, processor 760 may use the RTC to generate a time stamp that includes the measurement time of the first value. Further, in these embodiments, processor 760 use transmitter 740 to send the time stamp to remote apparatus or system 750.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. For example, advantageous results still could be if components in the disclosed systems were combined in a different manner and/or replaced or supplemented by other components. Other implementations are also within the scope of the following exemplary claims. The specification and drawings are accordingly to be regarded in an illustrative rather than restrictive sense. Moreover, it is intended that the disclosed embodiments and examples be considered as exemplary only, with a true scope of the present disclosure being indicated by the following claims and their equivalents.

What is claimed is:

1. A low-power measuring device comprising:
a first sensor configured to measure a first value, the first value being a measurement of a variable, wherein the variable comprises a voltage applied to an oscillator and the first sensor comprises a voltage sensor coupled to measure the voltage applied to the oscillator;
a counter unit including the oscillator, the counter unit configured to generate a first counter value indicative of a first elapsed time since the first value is measured by the first sensor, wherein a correlation between the first counter value and the first elapsed time varies based upon the variable, and wherein the correlation comprises a determined period of the oscillator used to convert the first counter value to the first elapsed time; and
at least one processor coupled to the first sensor and to the counter unit, the at least one processor configured to:
send the first value to a remote apparatus;
send the first counter value to the remote apparatus;
cause the remote apparatus to determine the first elapsed time based on the first value and the first counter value, wherein the remote apparatus adjusts the determined period of the oscillator used to determine the first elapse time based on changes in the first value; and
cause the remote apparatus to determine a first obtained time at which the first value is measured by the first sensor based on the first elapsed time and a reference time of the remote apparatus.

2. The low-power measuring device of claim 1, further comprising a second sensor, the second sensor including one of an electrochemical sensor, an optical sensor, or an electrical sensor.

3. The low-power measuring device of claim 1, further comprising a second sensor for measuring an analyte of bodily fluid, and wherein the at least one processor is further configured to send a measured analyte value from the second sensor to the remote apparatus.

4. The low-power measuring device of claim 3, wherein the second sensor is configured to measure the analyte at substantially the same time as the first value.

5. The low-power measuring device of claim 1, wherein the low-power measuring device is a body-mountable device.

6. The low-power measuring device of claim 1, wherein the low-power measuring device is a portable device and further comprises a battery.

7. The low-power measuring device of claim 1, further comprising a transmitter, and wherein the at least one processor causes the first value and the first counter value to be sent to the remote apparatus using the transmitter.

8. The low-power measuring device of claim 1, wherein the low-power measuring device is an implant device for complete or partial implantation in a body.

9. The low-power measuring device of claim 1, wherein the oscillator includes at least one of an RC oscillator, LC oscillator, or a micro-electro-mechanical systems (MEMS) oscillator.

10. A method for determining obtained times of received values, the method comprising the following operations performed by at least one processor:
receiving a first value from a measuring device, the first value representing a variable obtained by the measuring device, wherein the variable comprises a voltage applied to an oscillator;
receiving a first counter value from the measuring device, the first counter value being generated by a counter unit including the oscillator of the measuring device and indicative of a first elapsed time between a reference time and a first obtained time of the first value, wherein the first obtained time is a time at which the first value is obtained by the measuring device;
adjusting a correlation between the first counter value and the first elapsed time based upon changes in the variable and wherein the correlation comprises a determined period of the oscillator used to convert the first counter value to the first elapsed time;
determining the first elapsed time represented by the first counter value as a function of the first value and the correlation; and
determining the first obtained time of the first value based on the first elapsed time and the reference time.

11. The method of claim 10, further comprising:
receiving a second value from the measuring device, the second value representing the variable obtained by the measuring device at a different time than the first value;
receiving a second counter value from the measuring device, the second counter value being generated by the counter unit of the measuring device and indicative of a second elapsed time between the first obtained time of the first value and a second obtained time of the second value, the second obtained time being a second time at which the second value is obtained by the measuring device;
determining the second elapsed time represented by the second counter value as function of at least one of the first value and the second value; and
determining the second obtained time of the second value based on the determined second elapsed time and the first obtained time of the first value.

12. The method of claim 10, wherein the reference time is one of:
a time at which the first value is obtained by the measuring device,
a time at which the first value is transmitted by the measuring device,
a time at which the first value is retrieved from a memory of the measuring device, and
a time at which the first value is received from the measuring device.

13. The method of claim 10, wherein the oscillator includes at least one of an RC oscillator, LC oscillator, or a MEMS oscillator.

14. The method of claim 10, wherein the oscillator generates a periodic signal and the first counter value is a number of cycles of a periodic signal elapsed between the reference time and a first obtained time of the first value.

15. The method of claim 10, wherein the first counter value is approximately proportional to the first elapsed time.

16. The method of claim 10, wherein the first value and the first counter value are received wirelessly from the measuring device.

17. A monitoring system comprising:
- a storage medium that stores a set of instructions; and
- at least one processor that is configured by the set of instructions to:
    - receive a first measured value from a measuring device, the first measured value being a variable measured by the measuring device, wherein the variable comprises a voltage applied to an oscillator;
    - determine a received time representing when the first measured value is received from the measuring device;
    - receive a first counter value from the measuring device, the first counter value being generated by a counter unit including the oscillator of the measuring device and indicative of a first elapsed time between the received time and a first measurement time of the first measured value, the first measurement time being a time at which the first measured value is measured by the measuring device;
    - adjusting a correlation between the first counter value and the first elapsed time based upon changes in the variable and wherein the correlation comprises a determined period of the oscillator used to convert the first counter value to the first elapsed time;
    - calculate the first elapsed time represented by the first counter value as function of the first measured value and the correlation; and
    - calculate the first measurement time of the first measured value based on the first elapsed time and the received time.

* * * * *